(12) United States Patent  
Thiele

(10) Patent No.: US 7,648,461 B2  
(45) Date of Patent: Jan. 19, 2010

(54) USER INTERFACE FOR A THREE-DIMENSIONAL COLOUR ULTRASOUND IMAGING SYSTEM

(75) Inventor: Karl Thiele, Andover, MA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 385 days.

(21) Appl. No.: 10/559,215

(22) PCT Filed: Jun. 7, 2004

(86) PCT No.: PCT/IB2004/050856

§ 371 (c)(1),  
(2), (4) Date: Dec. 6, 2005

(87) PCT Pub. No.: WO2004/109330

PCT Pub. Date: Dec. 16, 2004

(65) Prior Publication Data

US 2006/0173326 A1    Aug. 3, 2006

Related U.S. Application Data

(60) Provisional application No. 60/477,206, filed on Jun. 10, 2003.

(51) Int. Cl.  
*A61B 8/00* (2006.01)

(52) U.S. Cl. .................. 600/453; 600/437; 600/439; 600/443; 600/448; 600/449; 600/458; 600/459; 600/466; 600/465; 600/461

(58) Field of Classification Search ......... 600/437–461; 382/128  
See application file for complete search history.

(56) References Cited

U.S. PATENT DOCUMENTS 5,315,999 A * 5/1994 Kinicki et al. ............. 600/443
5,957,138 A * 9/1999 Lin et al. .................. 600/453
5,993,390 A    11/1999 Savord et al.
5,997,479 A    12/1999 Savord et al.
6,013,032 A     1/2000 Savord
6,126,602 A    10/2000 Savord et al.

OTHER PUBLICATIONS

"Interactive Acquisition, Analysis, and Visualization of Sonographicvolume Data", by T.R. Nelson et al., International Journal of Imaging systems and Technology, Wiley & Sons, New York, pp. 26-37.

* cited by examiner

*Primary Examiner*—Brian Casler  
*Assistant Examiner*—John F Ramirez

(57) ABSTRACT

A three-dimensional ultrasound imaging system color user interface generates a volumetrically-rendered ultrasound image. The ultrasound image is manipulable using three-dimensional image compositing functions. The interface presents to the user three-dimensional image controls for controlling the ultrasound image. The three-dimensional image controls have an operational similarity to two-dimensional image controls for controlling a two-dimensional ultrasound image. The interface further relates the three-dimensional ultrasound image controls to the plurality of three-dimensional image compositing functions for manipulating the ultrasound images. Additionally, the interface presents to the user a three-dimensional color image control for controllably manipulating the ultrasound image using three-dimensional image using compositing functions such as a color flow mapping function, a color flow overlay function for mapping fluid flow direction, a depth-based velocity visualization color mapping function; and an absolute velocity representation function for mapping absolute fluid flow velocity relating to said ultrasound object.

10 Claims, 13 Drawing Sheets

FIG. 10

USER INTERFACE FOR A THREE-DIMENSIONAL COLOUR ULTRASOUND IMAGING SYSTEM

CROSS REFERENCE TO RELATED APPLICATION

This application claims the benefit of U.S. provisional application Ser. No. 60/477,206 filed Jun. 10, 2003, which is incorporated herein by reference.

The present invention relates to ultrasound imaging systems and their methods of operation and, in particular, to a three-dimensional ultrasound imaging system color user interface.

Diagnostic ultrasound equipment transmits sound energy into the human body and receives signals reflecting off tissue and organs such as the heart, liver, kidney, etc. Blood flow patterns are obtained from Doppler shifts or shifts in time domain cross correlation functions due to blood cell motion. These produce reflected sound waves and generally may be displayed in a two-dimensional format known as color flow imaging or color velocity imaging. The ultrasound imaging system emits pulses over a plurality of paths and converts echoes received from objects on the plurality of paths into electrical signals used to generate ultrasound data from which an ultrasound image can be displayed. The process of obtaining the raw data from which the ultrasound data is produced is typically termed "scanning," "sweeping," or "steering a beam". Generally, the amplitudes of reflected components for structures, such as the heart or vessel walls, have lower absolute velocities and are 20 dB to 40 dB (10-100 times) larger than the amplitudes of reflected components for blood cells.

Real-time sonography refers to the presentation of ultrasound images in a rapid sequential format as the scanning occurs. Scanning is either performed mechanically (by physically oscillating one or more transducer elements) or electronically. By far, the most common type of scanning in modem ultrasound systems is electronic scanning wherein a group of transducer elements (termed an "array") arranged in a line are excited by a set of electrical pulses, one pulse per element, timed to construct a sweeping action.

Many presently used three-dimensional ultrasound imaging methods and systems use an ultrasound probe to acquire a series of two-dimensional planes of data or tomographic data slices through the human body. The associated imaging electrodes tag these tomographic data slices with positional information related to the two-dimensional probe. These tagged slices are acquired using one of a variety of acquiring techniques, such as using a video grabber. The video grabber, for example, takes the ultrasound image from the display on the two-dimensional ultrasound machine. These images may then be sent to an off-line device for subsequent volume reconstruction.

Problems in fully using these and other ultrasound imaging techniques relate to the difficulties of using time gating techniques for acquiring images of repetitive moving structures in the body, especially of the heart. In particular, there are both operational and programming complexities associated with porting these two-dimensional data slices to three-dimensional offline programs. The time needed to manipulate and to visualize this data, particularly when using off-line computer programs, is excessive. Moreover, the data is oftentimes difficult to use and interpret.

Even for those with the skills to operate three-dimensional ultrasound imaging systems, an important problem still exists with the data manipulation controls of known ultrasound imaging systems. For example, heretofore the controls for color three-dimensional imaging systems are unique to three-dimensional systems. Not only are these controls difficult to master, but also they are non-intuitive to those trained in scanning and evaluating two-dimensional ultrasound images. This is particularly true for those systems displaying color Doppler information. Due to the complexities in understanding and using the three-dimensional data, as well as those of using the associated volume rendering programs, only a small number of clinicians and researchers have mastered three-dimensional ultrasound systems. This has significantly limited the practical use and associated benefits of three-dimensional volume-rendering ultrasound imaging systems.

At the technical level, certain functional limitations also exist in the use of three-dimensional volumetrically rendered ultrasound data. For example, known interfaces generally display color Doppler (e.g., blood velocity information) in conjunction with the anatomical black and white (BW) information. This results in an interaction between the BW and color controls. In essence, this creates a situation where a BW voxel and a color voxel, both relating to the same space-time location of an ultrasound object, such as a human heart, would compete against one another to be visualized by a user.

Accordingly, there is a need for improved quantity in the system controls for visualizing three-dimensional volumetrically-rendered color ultrasound imaging data.

A further need exists to address the problem that known three-dimensional ultrasound imaging systems fail to present to a user, particularly a user skilled in sonography, neither highly intuitive controls nor readily understandable responses to these controls.

Still further, there is a need for reducing the potentially adverse effects of interaction between system controls when producing and analyzing three-dimensional volumetrically rendered ultrasound data Such interactions may occur, for example, in the generation and use of BW and color data.

In accordance with the present invention, an improved three-dimensional ultrasound imaging system color user interface for using a real-time, three-dimensional, volume rendering ultrasound imaging system is provided that substantially eliminates or reduces the disadvantages and problems associated with prior ultrasound image system display and interface systems.

According to one aspect of the present invention, there is provided a method for interfacing a three-dimensional ultrasound imaging system with a user. The method includes the steps of generating a three-dimensional volumetrically-rendered ultrasound image of an ultrasound object. The three-dimensional volumetrically-rendered ultrasound image is manipulable using a plurality of three-dimensional image compositing functions. The method further presents to the user a plurality of three-dimensional image controls for controlling the three-dimensional volumetrically-rendered ultrasound image. The three-dimensional image controls have an operational similarity to two-dimensional image controls for controlling a two-dimensional ultrasound image. Further, the method includes the step of relating the plurality of three-dimensional ultrasound image controls to the plurality of three-dimensional image compositing functions for manipulating the three-dimensional volumetrically-rendered ultrasound image of the ultrasound object.

An additional feature of this aspect of the invention includes the steps of first presenting a plurality of three-dimensional image responses from operation of said three-dimensional ultrasound image controls. The image responses are similar to image responses of a two-dimensional ultrasound imaging system. This feature further includes the step of controlling the three-dimensional volumetrically-rendered ultrasound image using the three-dimensional compositing functions.

According to another aspect of the invention, there is provided here a method for interfacing a three-dimensional ultrasound imaging system with a user that begins with generating a three-dimensional volumetrically-rendered ultrasound image of fluid flow relating to an ultrasound object. The three-dimensional volumetrically-rendered ultrasound image is manipulable using a plurality of three-dimensional image compositing functions. The method presents to the user a three-dimensional color image control for controllably manipulating the three-dimensional volumetrically-rendered ultrasound image using the plurality of three-dimensional image compositing functions. The three-dimensional image compositing functions are selected from a group of such functions. The group of compositing functions includes essentially (1) a color flow mapping function for mapping fluid flow relating to said ultrasound object; (2) a color flow overlay function for mapping fluid flow direction relating to said ultrasound object; (3) a depth-based velocity visualization color mapping function for mapping fluid flow depth relating to said ultrasound object; and (4) an absolute velocity representation function for mapping absolute fluid flow velocity relating to said ultrasound object.

A variety of further features relate to this aspect of the invention. For example, one further feature includes the step of presenting to the user the color flow overlay function for mapping fluid flow direction relating to said ultrasound object as an overlay function of overlaying forward and reverse flows. This feature permits generating in real-time color combinations arising from the overlaying function. Another further feature includes the step of presenting to the user the depth-based velocity visualization color mapping function using a light color for showing physically closer velocities relative to a predetermined observation point and a dark color associates with physically farther velocity away from said observation point. A still further feature of this aspect includes presenting to the user the absolute velocity representation function using absolute velocity to represent the structure, size and position of flow pathologies associated with said ultrasound object.

A technical advantage of the present invention relates to the making much easier the use of two-dimensional color Doppler controls for the operation of and analysis supported by three-dimensional ultrasound imaging systems. The present invention provides effective ways to control complex three-dimensional compositing functions so that their behavior is quite similar to how such a user has generally operated and generated analytical information in two-dimensional color imaging systems.

One more technical advantage of the present invention is a reduction of the adverse effects of interaction between system controls when producing and analyzing three-dimensional volumetrically rendered ultrasound data. The present invention provides the ability to selectively suppress or eliminate the interaction between BW and color data. The method and system of the present invention provide a user interface that contemplates and effectively handles these potentially adverse technical interactions.

A further technical advantage of the present invention is that of providing a system in which there is combined into a single control a set of three-dimensional complex functions and capabilities for substantially enhancing the use and visualization of ultrasound measurements. In a preferred embodiment, this control is referred to as "C Vision," and contains four separate three-dimensional ultrasound imaging modes.

For example, the present invention may be viewed as providing a "fly-by-wire" capability whereby the user, through a single and simple interface, may affect numerous complex parameters and algorithms that generate three-dimensional volumetrically-rendered ultrasound images. Particularly important to this technical advantage is that the present invention conceals from the user the inherent complexities of achieving these multiple image compositing functions. As a result, those trained in the use of two-dimensional ultrasound systems, as well as new users, will find the benefits of real-time, three-dimensional, volumetrically-rendered ultrasound images much more readily accessible.

Other technical advantages of the present invention are readily apparent to one skilled in the art from the following figures, description, and claims.

For a more complete understanding of the present invention and advantages thereof, reference is now made to the following description which is to be taken in conjunction with the accompanying drawings in which like reference numbers indicate like features and wherein.

Figure 4:
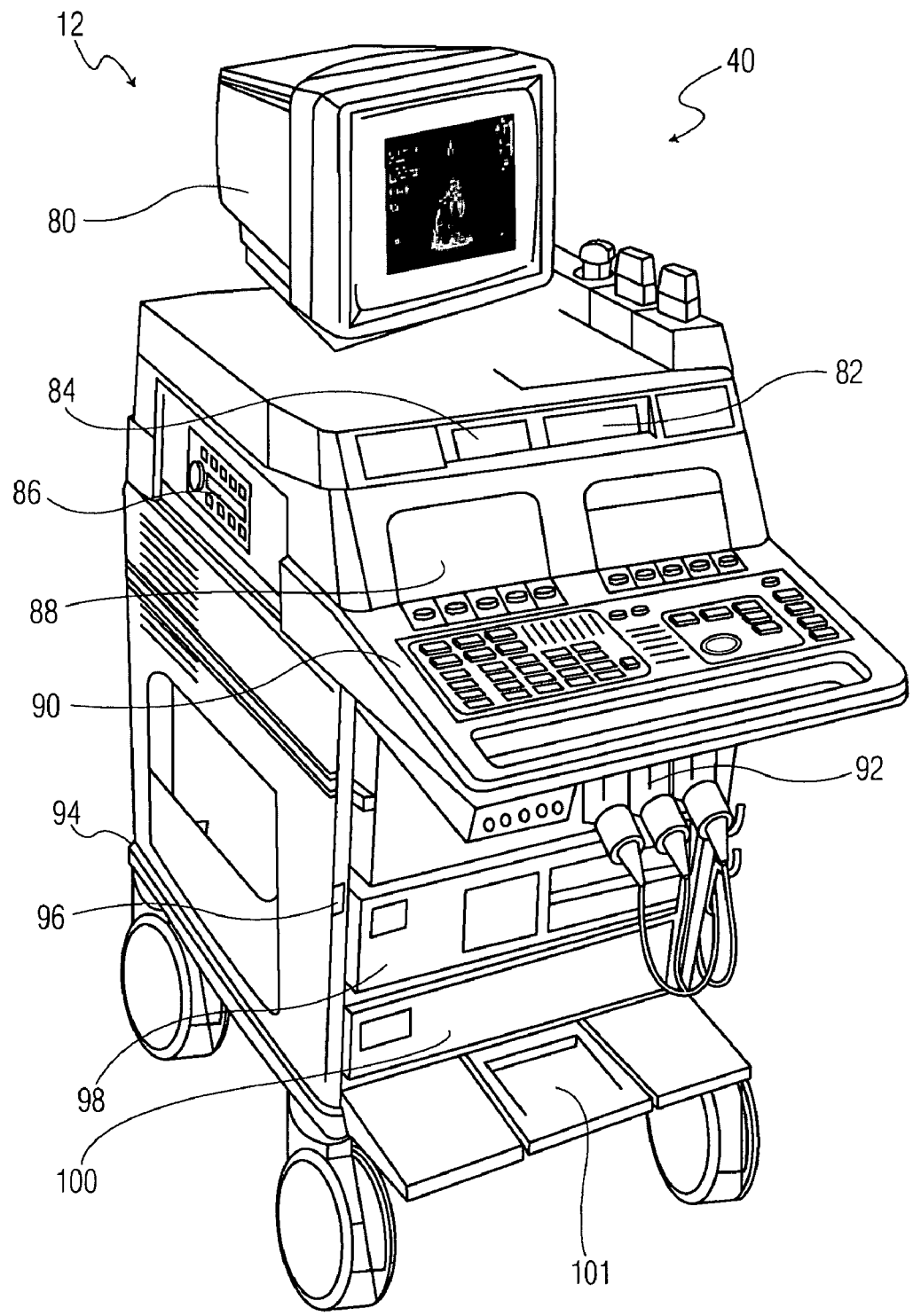
Figure 5:
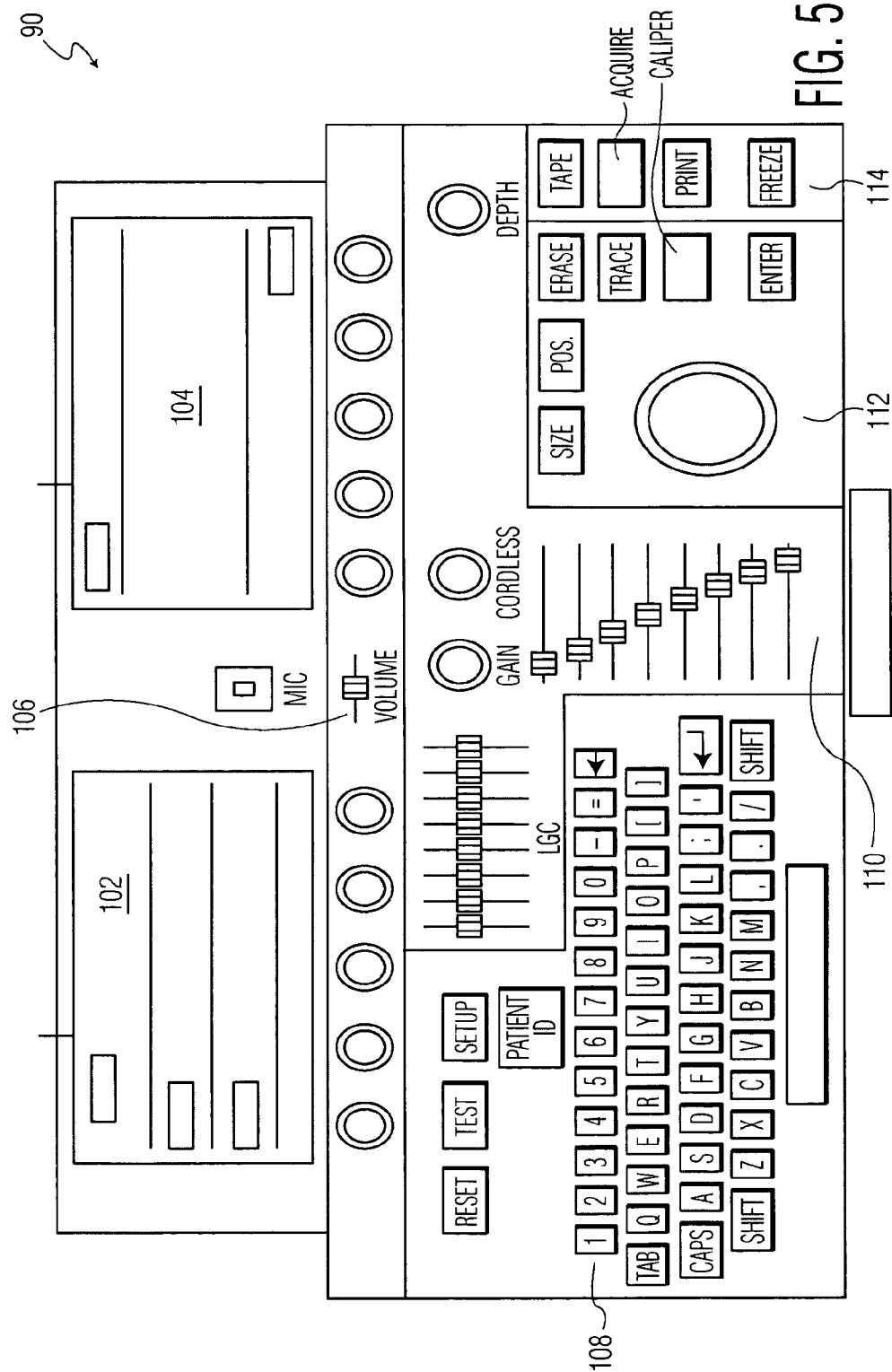
Figure 6:
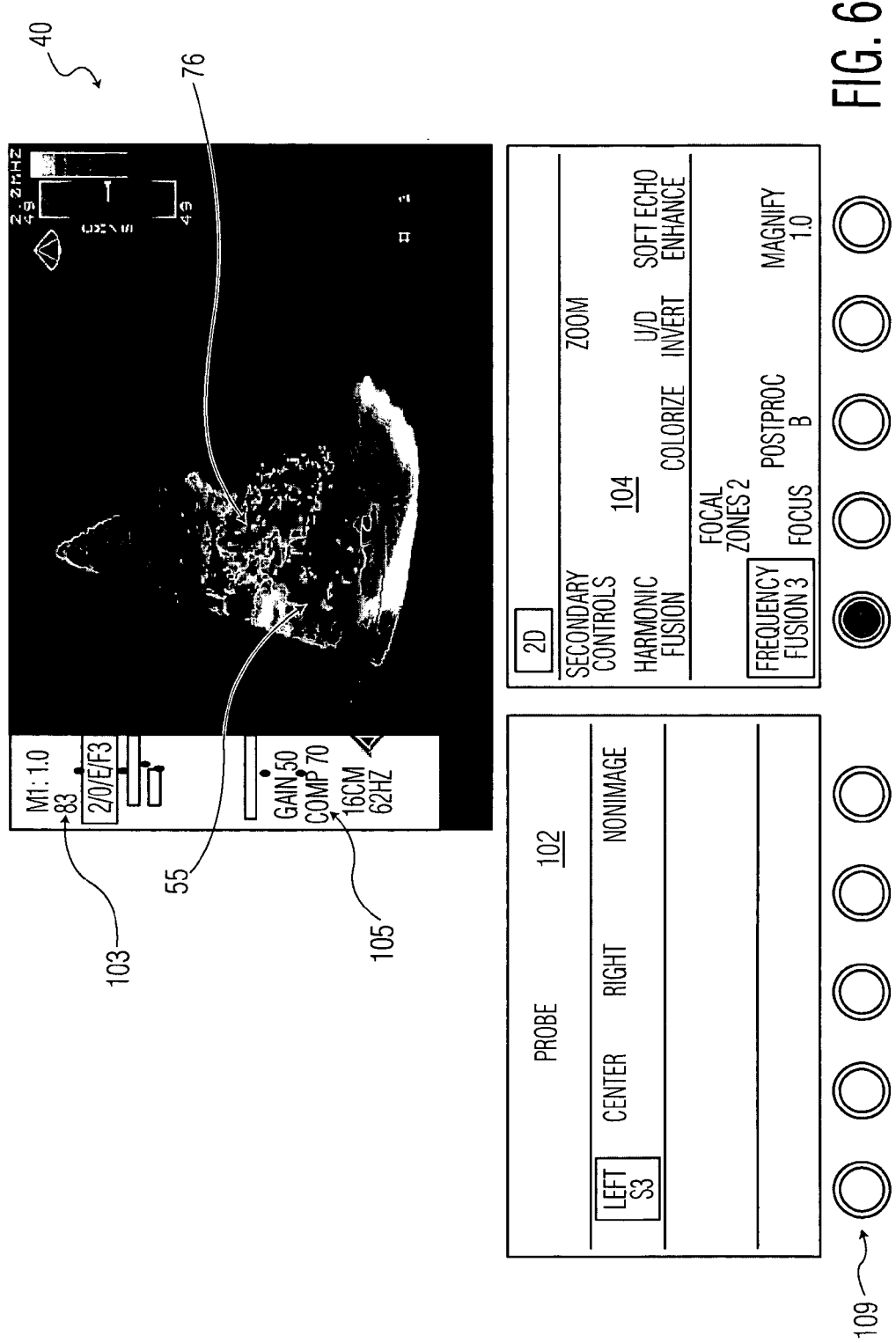
Figure 7:
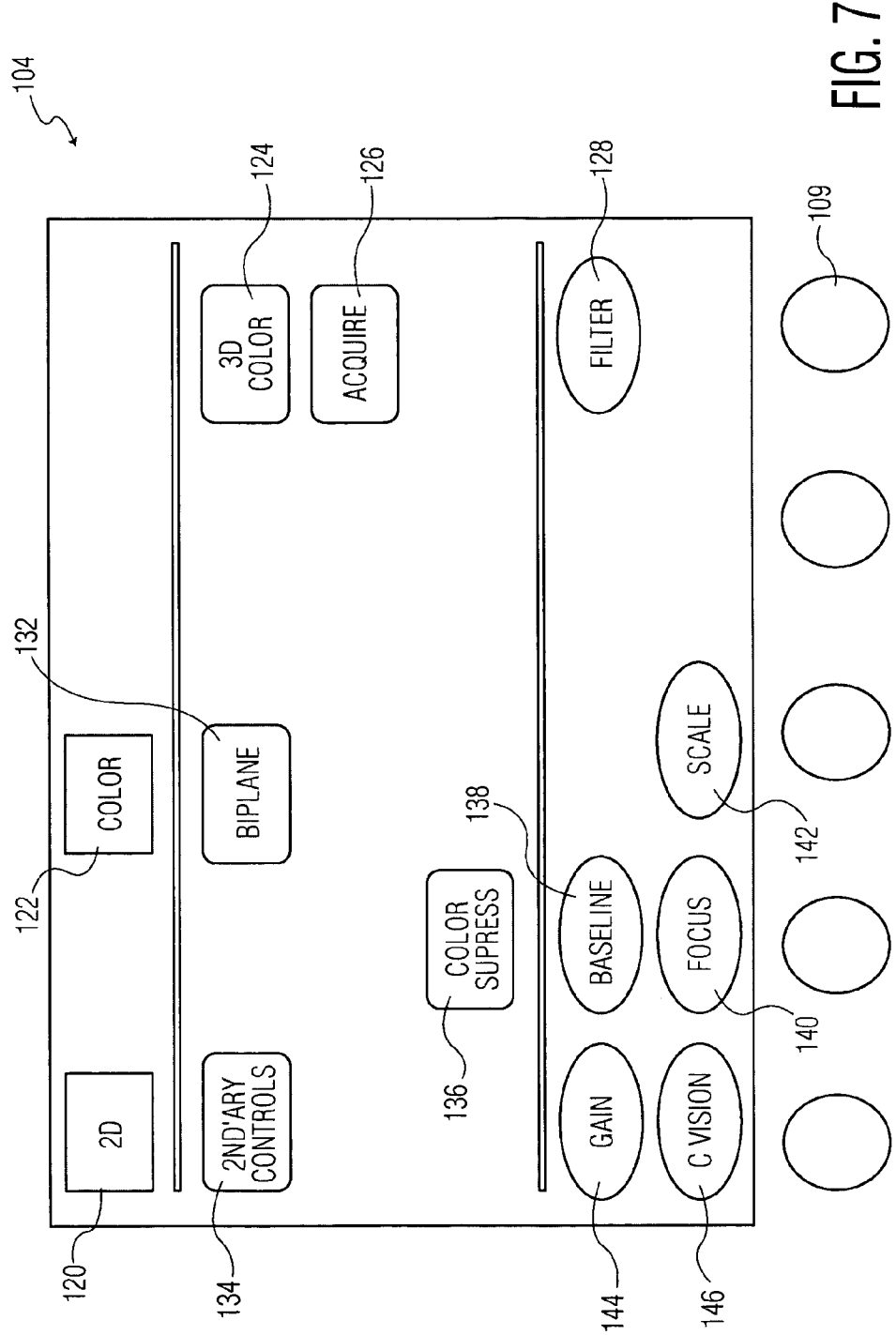
Figure 8:
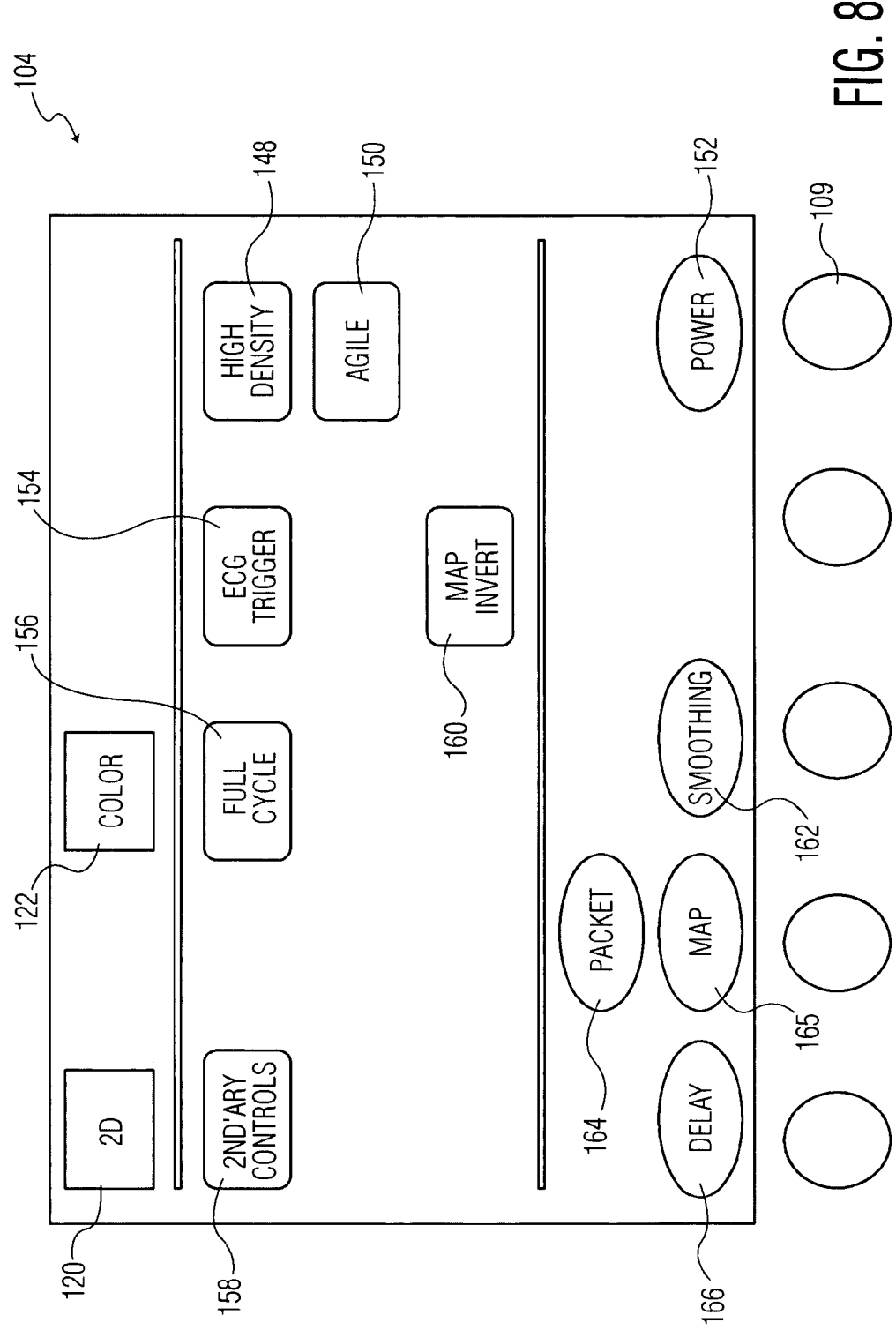
Figure 9:
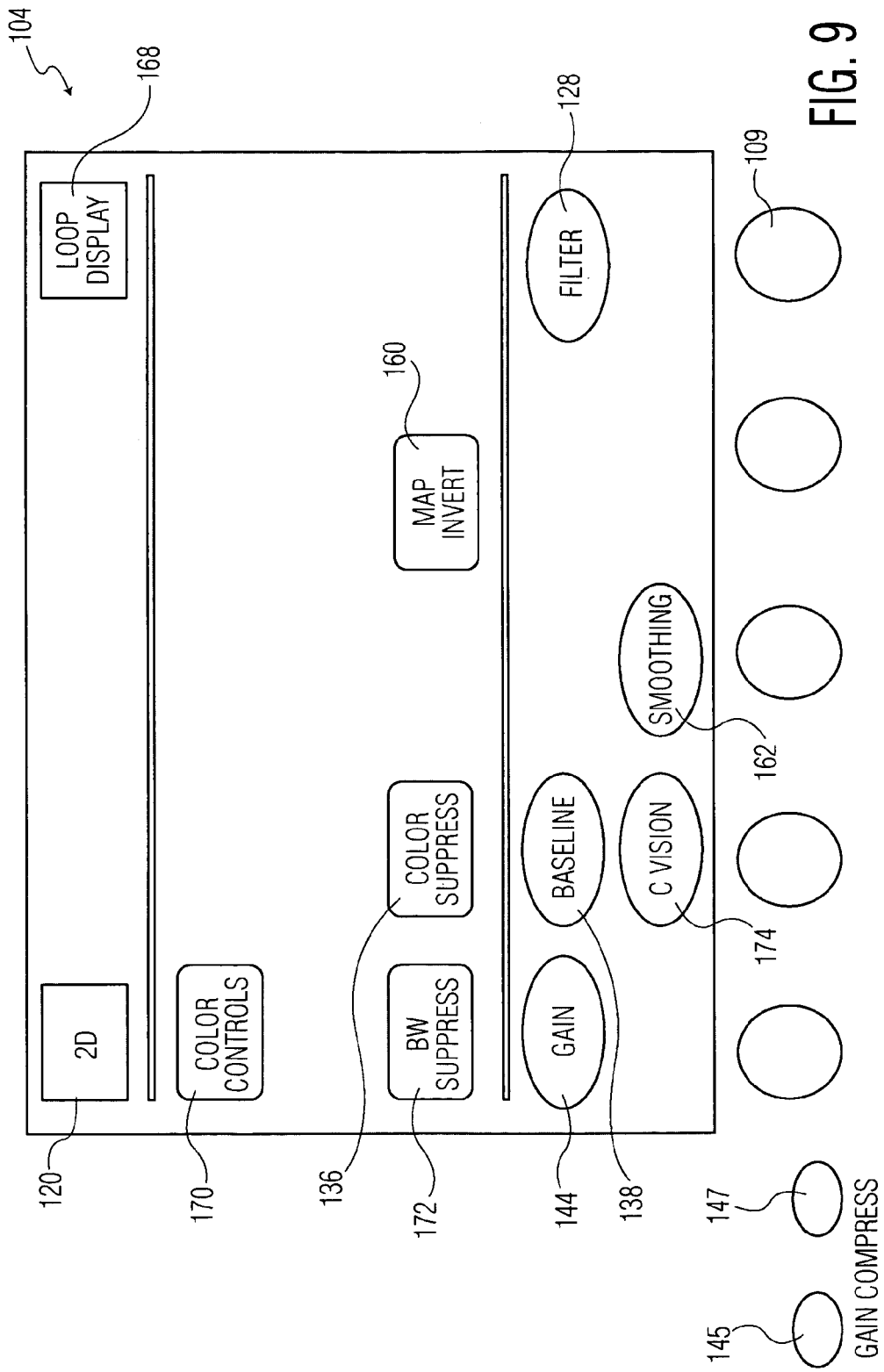

FIG. 4 portrays a view of a three-dimensional volumetric rendering ultrasound imaging system console according to the teachings of the present invention;

FIG. 5 presents the control panel for the ultrasound imaging system of FIG. 4;

FIG. 6 shows the control touch panels for implementing the present invention using an ultrasound imaging system;

FIGS. 7, 8 and 9 depict touch screen arrangements for achieving various aspects of the present invention;

Figure 10:
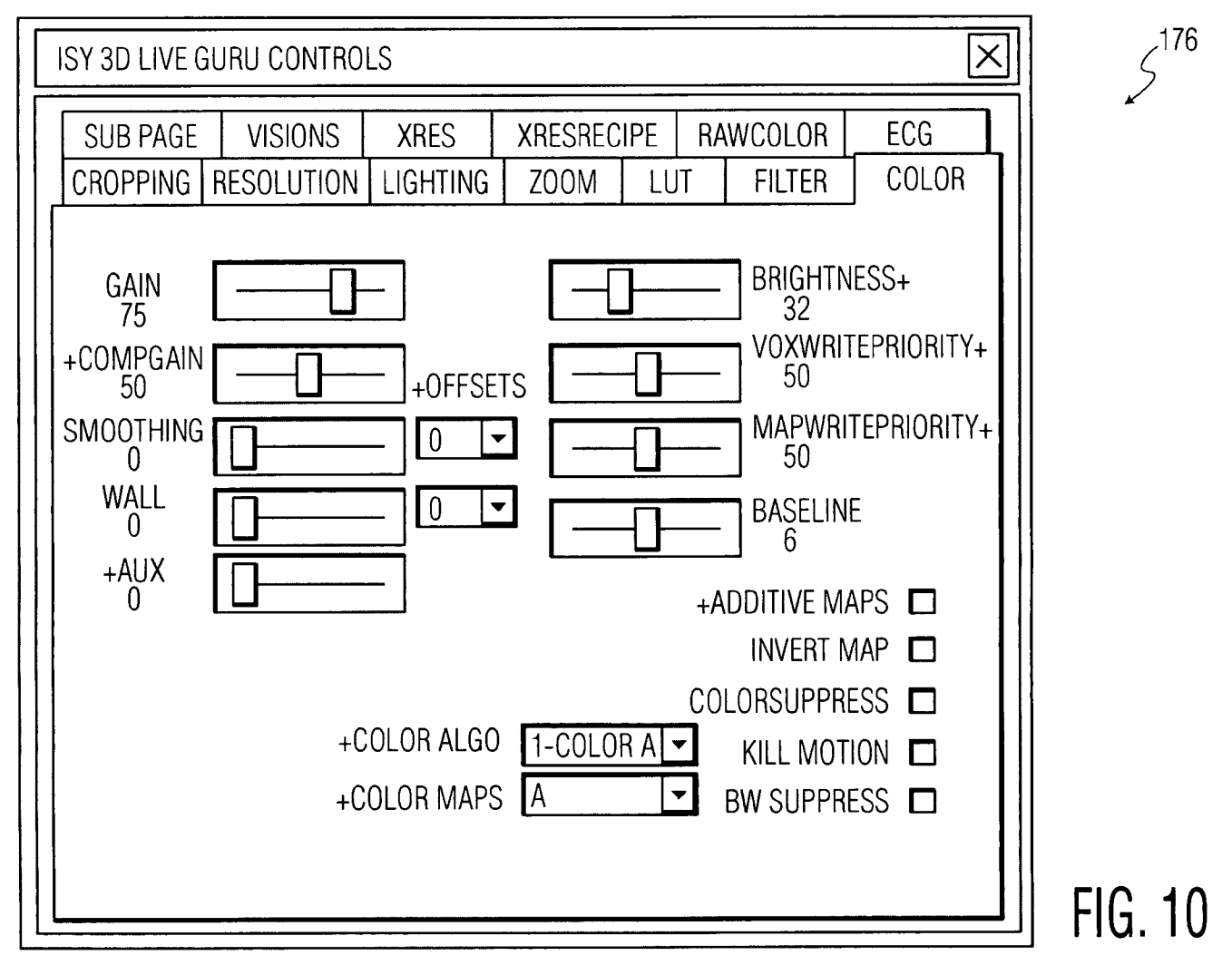

FIG. 10 depicts the numerous complex controls that are hidden and made transparent to the user through the use of the present invention; and FIGS. 11 through 15 provide monitor displays for demonstrating the various functions and capabilities of the present invention.

The preferred embodiment of the present invention and its advantages are best understood by referring to FIGS. 1 through 15 of the drawings, like numerals being used for like and corresponding parts of the various drawings.

Figure 1:
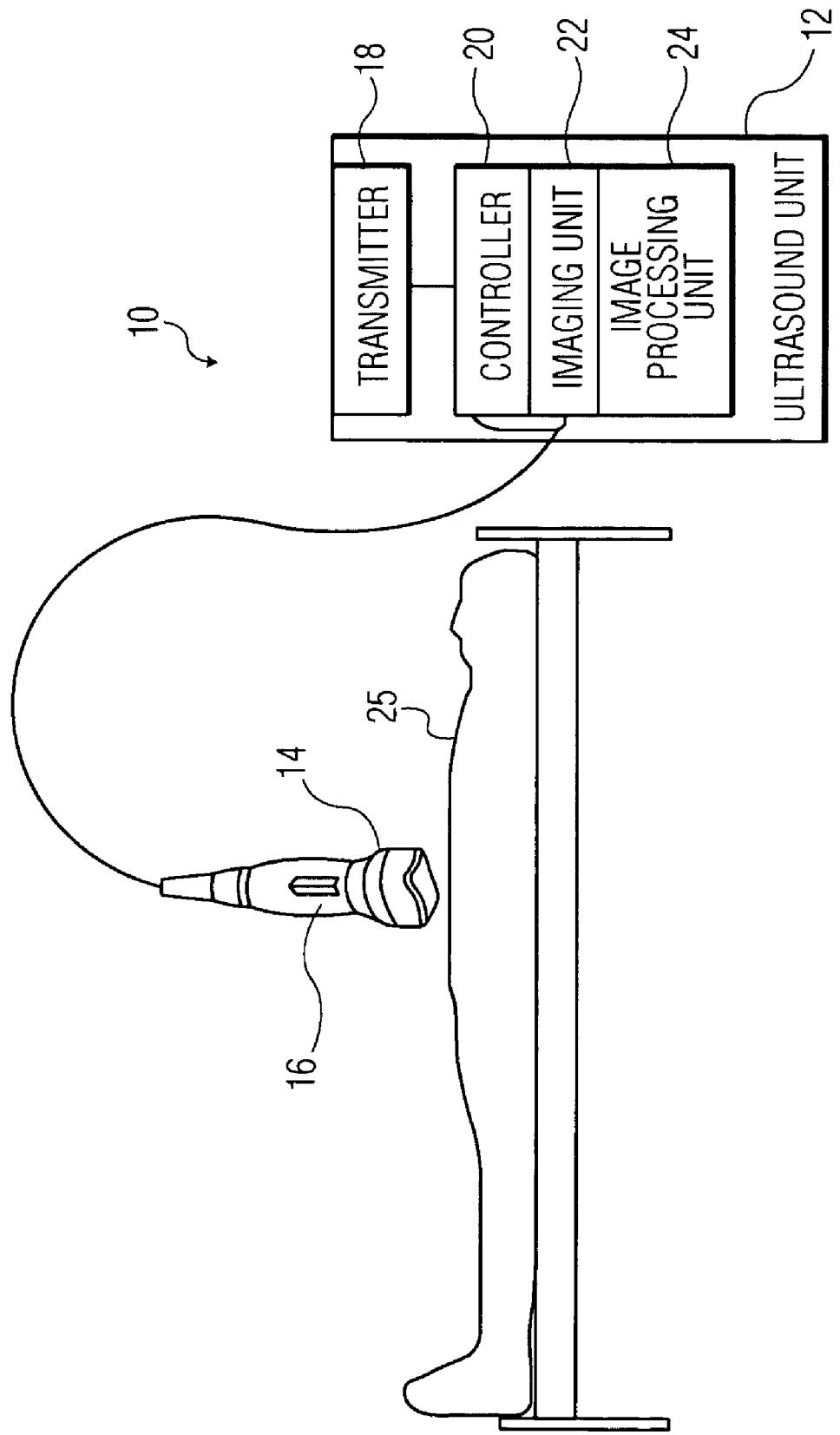
FIG. 1 is a diagram illustrating the use of an ultrasound diagnostic system that may use the present invention.

FIG. 1 shows a simplified block diagram of an ultrasound imaging system 10 that may use the concepts presented in accordance with the preferred embodiment of the present invention. It will be appreciated by those of ordinary skill in the relevant arts that ultrasound imaging system 10, as illustrated in FIG. 1, and the operation thereof as described hereinafter is intended to be generally representative of such systems and that any particular system may differ significantly from that shown in FIG. 1, particularly in the details of construction and operation of such system. As such, ultrasound imaging system 10 is to be regarded as illustrative and exemplary and not limiting as regards the invention described herein or the claims attached hereto.

In this specification the word "system" is to be understood as generic to including one element or device and to include multiple elements and/or devices. Also, in this specification the word "mode" is to be understood as generic to functions of, operations performed by, operations performed on, and/or settings of the entire ultrasound system or of any part of the ultrasound system. Therefore, the description that follows of the exemplary embodiments is for purposes of illustration and not limitation.

In certain circumstances, when it is desirable that a piece of hardware possess certain characteristics, these characteristics are described more fully in the following text. The required structures for a variety of these machines may appear in the description given below. Machines which may be modified in accordance with the teachings of the present invention include those manufactured by such companies as PHILIPS MEDICAL SYSTEMS INTERNATIONAL, GE MEDICAL SYSTEMS, and SIEMANS MEDICAL SYSTEMS, as well as other manufacturers of ultrasound equipment.

In FIG. 1, Ultrasound imaging system 10 generally includes ultrasound unit 12 and connected transducer 14. Transducer 14 includes a receiver 16. Ultrasound unit 12 has integrated therein a transmitter 18 and associated controller 20. Controller 20 provides overall control of the system by providing timing and control functions. As will be discussed in detail below, the control routines include a variety of routines that modify the operation of receiver 16 so as to produce a volumetric ultrasound image as a live real-time image, a previously recorded image, or a paused or frozen image for viewing and analysis.

Figure 2:
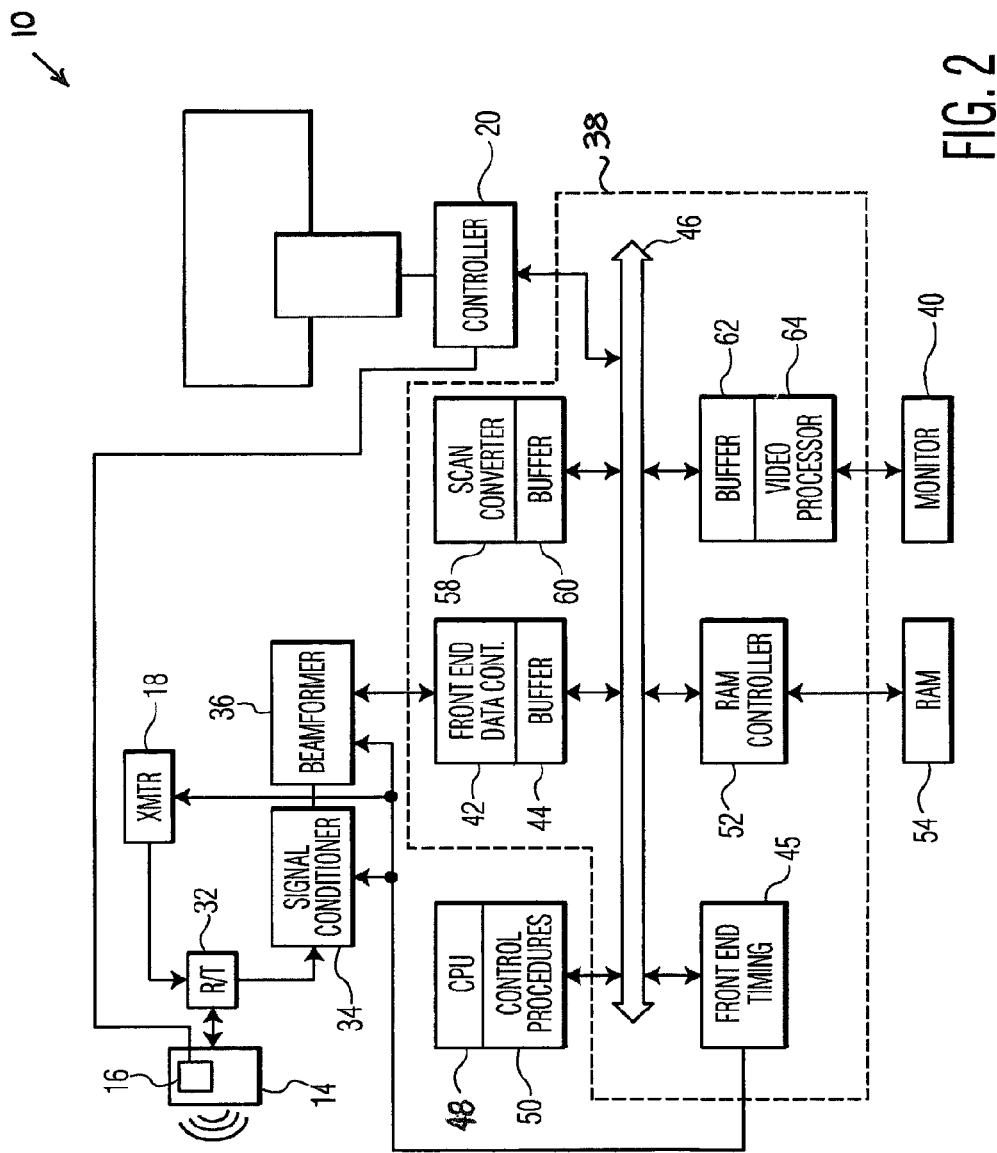
FIG. 2 is a block diagram of an ultrasound system in accordance with the preferred embodiment of the present invention.

Ultrasound unit 12 is also provided with imaging unit 22 for controlling the transmission and receipt of ultrasound, and image processing unit 24 for producing a display on a monitor (See FIG. 2). Image processing unit 24 contains routines for rendering a three-dimensional image.

During freehand imaging, a user moves transducer 14 over subject 25 in a controlled motion. Ultrasound unit 12 combines image data produced by imaging unit 22 with location data produced by the controller 20 to produce a matrix of data suitable for rendering onto a monitor (See FIG. 2). Ultrasound imaging system 10 integrates image rendering processes with image processing functions using general purpose processors and PC-like architectures. On the other hand, use of ASICs to perform the stitching and rendering is possible.

FIG. 2 is a block diagram of an ultrasound system 10 in accordance with the preferred embodiment of the present invention. The ultrasound imaging system 10 shown in FIG. 2 is configured for the use of pulse generator circuits, but could be equally configured for arbitrary waveform operation. Ultrasound imaging system 10 uses a centralized architecture suitable for the incorporation of standard personal computer ("PC") type components and includes transducer 14 which, in a known manner, scans an ultrasound beam, based on a signal from a transmitter 18, through an angle. Backscattered signals, i.e., echoes, are sensed by transducer 14 and fed, through receive/transmit switch 32, to signal conditioner 34 and, in turn, to beamformer 36. Transducer 14 includes elements, preferably configured as an electronically steerable two-dimensional array. Signal conditioner 34 receives backscattered ultrasound signals and conditions those signals by amplification and forming circuitry prior to their being fed to beam former 36. Within beam former 36, ultrasound signals are converted to digital values and are configured into "lines" of digital data values in accordance with amplitudes of the backscattered signals from points along an azimuth of the ultrasound beam.

Beamformer 36 feeds digital values to application specific integrated circuit (ASIC) 38 which incorporates the principal processing modules required to convert digital values into a form more conducive to video display that feeds to monitor 40. Front end data controller 42 receives lines of digital data values from beam former 36 and buffers each line, as received, in an area of buffer 44. After accumulating a line of digital data values, front end data controller 42 dispatches an interrupt signal, via bus 46, to shared central processing unit (CPU) 48, which may be a MOTOROLA PowerPC. CPU 48 executes control procedures 50 including procedures that are operative to enable individual, asynchronous operation of each of the processing modules within ASIC 38. More particularly, upon receiving an interrupt signal, CPU 48 feeds a line of digital data values residing in buffer 44 to random access memory (RAM) controller 52 for storage in random access memory (RAM) 54 which constitutes a unified, shared memory. RAM 54 also stores instructions and data for CPU 48 including lines of digital data values and data being transferred between individual modules in ASIC 38, all under control of RAM controller 52.

Transducer 14, as mentioned above, incorporates receiver 16 that operates in connection with transmitter 18 to generate location information. The location information is supplied to (or created by) controller 20 which outputs location data in a known manner. Location data is stored (under the control of the CPU 48) in RAM 54 in conjunction with the storage of other digital data values.

Control procedures 50 control front end timing controller 45 to output timing signals to transmitter 28, signal conditioner 34, beam former 36, and controller 20 so as to synchronize their operations with the operations of modules within ASIC 38. Front end timing controller 45 further issues timing signals which control the operation of the bus 46 and various other functions within the ASIC 38.

As aforesaid, control procedures 50 configure CPU 48 to enable front end data controller 42 to move the lines of digital data values and location information into RAM controller 52 where they are then stored in RAM 54. Since CPU 48 controls the transfer of lines of digital data values, it senses when an entire image frame has been stored in RAM 54. At this point, CPU 48 is configured by control procedures 50 and recognizes that data is available for operation by scan converter 58. At this point, therefore, CPU 48 notifies scan converter 58 that it can access the frame of data from RAM 54 for processing.

To access the data in RAM 54 (via RAM controller 52), scan converter 58 interrupts CPU 48 to request a line of the data frame from RAM 54. Such data is then transferred to buffer 60 of scan converter 58 and is transformed into data that is based on an X-Y coordinate system. When this data is coupled with the location data from controller 20, a matrix of data in an X-Y-Z coordinate system results. A four-(4-) dimensional matrix may be used for 4-D (X-Y-Z-time) data. This process is repeated for subsequent digital data values of the image frame from RAM 54. The resulting processed data is returned, via RAM controller 52, into RAM 54 as display data. The display data is stored separately from the data produced by beam former 36. CPU 48 and control procedures 50, via the interrupt procedure described above, sense the completion of the operation of scan converter 58. Video processor 64, such as the MITSUBISHI VOLUMEPRO series of cards, interrupts CPU 48 which responds by feeding lines of video data from RAM 54 into buffer 62, which is associated with the video processor 64. Video processor 64 uses video data to render a three-dimensional volumetric ultrasound image as a two-dimensional image on monitor 40. Further details of the processing of three dimensional cardiac data may be found in U.S. Pat. No. 5,993,390.

Figure 3:
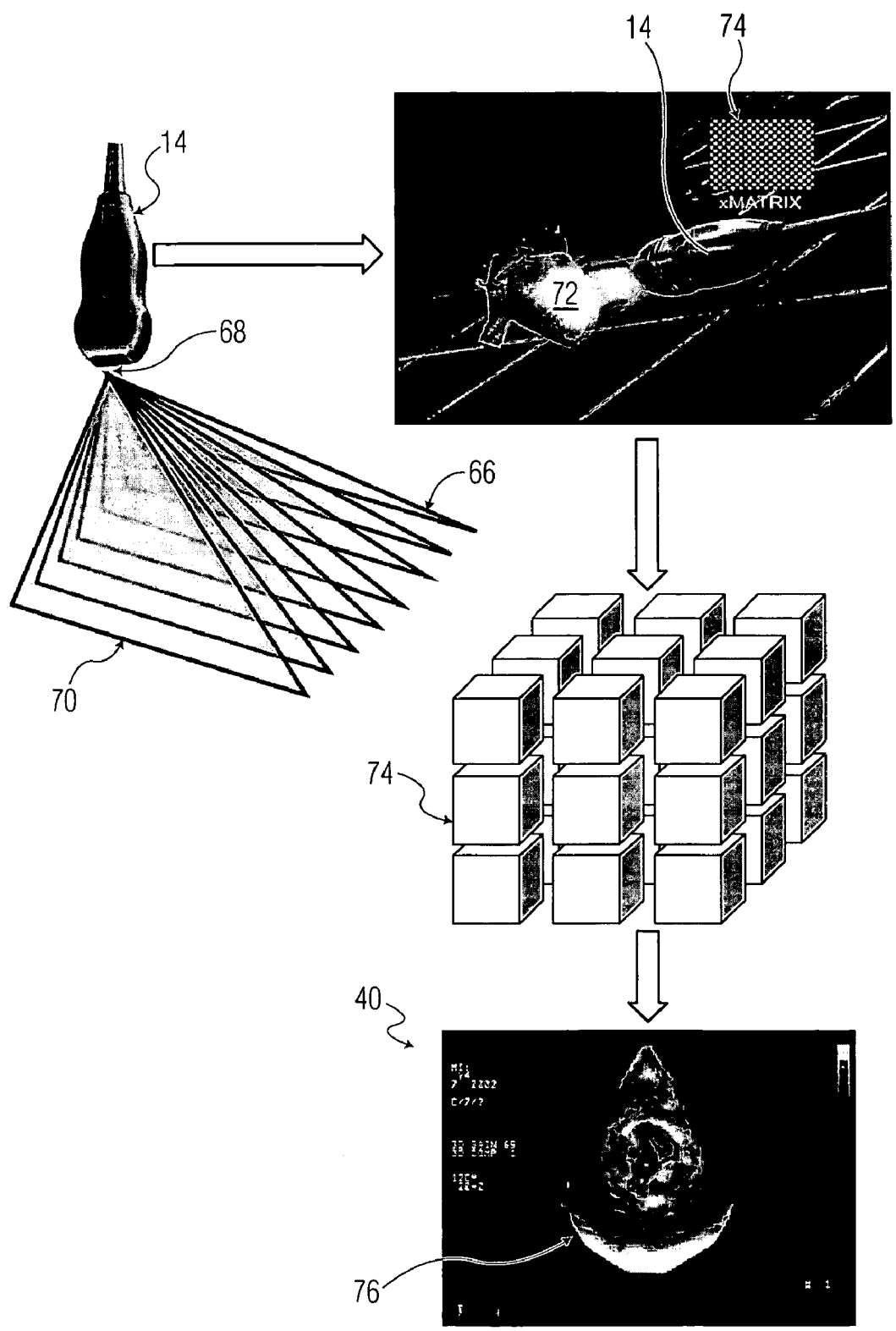
FIG. 3 shows conceptually the process of the present invention, beginning with ultrasound propagation and continuing through to display of a volumetric ultrasound image on a computer monitor.

FIG. 3 shows conceptually the ultrasound imaging process of the present invention, beginning with ultrasound propagation and continuing through to the display of a volumetric ultrasound image on computer monitor 40. In the example shown in FIG. 3, there are slices 66 conjoined at single apex 68, but otherwise separated. Each of scan lines 70 in slices 66 has a matching (or "indexed") scan line in the other slices. Preferably, scan lines 70 with the same lateral position are matched across the set of slices. One way to accomplish this is to index each of the scan lines in a slice by numbering them in sequence. Then scan lines 70 having the same index value can be easily matched.

To render a volumetric three-dimensional image, data points on each of sets of matched scan lines 70 are linearly combined using an addition routine. In other words, each slice in the set of slices is accumulated in the elevation direction to produce an aggregate slice for subsequent display. Preferably, but not necessarily, the data points in each slice are weighted, for example, on a line-by-line basis by using a multiply and accumulate routine (also known as a "MAC routine").

FIG. 3 further illustrates the processing of ultrasound data, for example of human heart 72, using volumetric ultrasound processing for which the present invention has particular beneficial application. In one embodiment, the present invention has particularly beneficial use with a live, three-dimensional ultrasound architecture that instantaneously processes data from slice 66 arising from the use of transducer 14 to produce voxel matrix 74 of data. Voxel matrix 74, through the use a powerful supercomputer architecture such as that of the SONOS 7500 System manufactured by Philips Medical Systems, processes within a small amount of time, nominally 50 milliseconds, streaming three-dimensional ultrasound data. This processed ultrasound data may then appear on a monitor screen 40 to show in real-time, volumetrically-rendered ultrasound object 76.

A three-dimensional system such as the SONOS 7500 with which the present invention operates uses transducer 14, which includes a 3000-element array, and associated microprocessors that preprocess data using an advanced, yet PC-based, computing platform, as well as special software that allows interactive image manipulation and an easy-to-use operator interface. The 3000-element array captures data about an ultrasound object, such as the heart, as a volume. By combining a transducer crystal that is etched to have the necessary number of crystals with a microprocessing circuit that efficiently triggers the transducer elements, the ultrasonic imaging system with which the present invention operates harnesses the computing power of more than 150 computer boards. Further details of such an array and microprocessors are described in U.S. Pat. Nos. 5,997,479; 6,013,032; and 6,126,602.

The processing architecture includes both hardware and software that allows real-time generation of volume data. This PC-based technology supports instantaneous display of three-dimensional images. With this technology, the ultrasound imaging system applies the 3000 channels to the SONOS 7500 mainframe beam former for scanning in real time. Three-dimensional scan converter 58 (FIG. 2) processes at a rate of over 0.3 giga-voxels per second to produce image 76 from voxel matrix 74.

The present embodiment of the invention, therefore, may be employed in a three-dimensional live ultrasound imaging and display process to enhance known echocardiography analysis and diagnosis. The system with which the present invention may operate has the ability to generate and display three-dimensional images of a beating heart an instant after the data are acquired. However, the present invention may also operation with other, near-real-time three-dimensional systems which may need several seconds to acquire the data and additional time to reconstruct it as a three-dimensional ultrasound display. In such systems, data acquisition leading to three-dimensional ultrasound images of the heart may be gated for electrocardiogram and respiration analysis and diagnosis.

The system with which the present invention preferably operates delivers a full-volume view of the heart that can be rotated to allow the operator to see cardiac anatomy from several perspectives. Images can also be cropped to obtain cross-sectional pictures of complex anatomical features such as heart valves. The preferred ultrasound system for using the present invention can also provide information about a patient's heart size, shape, and anatomic relationships. Such a system is attractive to a wide range of medical environments from the community hospital and university echo lab to private offices. The three-dimensional capability of such a system allows a better appraisal of the correlation between valves, chambers, and vessels in the heart.

The live, volumetric ultrasound system with which the present invention preferably operates provides improved visualization of complex anatomic features, particularly in pediatrics. Typically in pediatrics, cardiologists spend quite a bit of time looking at various two-dimensional planes, trying to link one part of the heart to another. Volume rendering by a system such as that of the present invention may lead to improved, faster assessment of the pediatric heart, because physicians can better visualize the heart and surrounding structures.

FIG. 4 portrays an isometric (isometric=?) view of a three-dimensional volumetric rendering ultrasound imaging system console 12 for employing the teachings of the present invention. In FIG. 4, ultrasound imaging console 12 includes monitor 40 which displays the three-dimensional volumetrically rendered ultrasound image 76 for a user to manipulate in the ultrasound diagnosis of patient 25. Ultrasound imaging system console 12 may include optical disk drives 82, floppy disk drive 84, VCR 86, touch panels 88 (including left touch panel 102 and right touch panel 104 described below), and keyboard controls 90. Electrical connections associated with ultrasound imaging system console 12 include transducer connections 92, circuit breaker 94 on back side of console 12, and main power switch 96. For purposes of the present invention, ultrasound imaging system console 12 provides optional peripheral slot 98 and accommodates the three-dimensional volumetric imaging module 120, as herein further described. Wheel lock 101 appropriately holds ultrasound imaging system console 12 in position as the user takes ultrasound measurements. The discussion that follows will lead to an explanation of the control system, include a variety of switches, levers, and touch panel screens for controlling a system such as ultrasound imaging system 10 through the interface with imaging system console 12.

As FIG. 5 shows, ultrasound imaging system console 12 includes touch panels 88 and keyboard controls 90 for control of three-dimensional volumetrically rendered ultrasound image 76 on monitor 40. These include primary touch panel 102 and secondary touch panel 104, volume control switch 104, and alphanumeric keyboard 106. Moreover, console 90 includes image tuning controls 110, and measurement and trackball controls 112, and hardcopy and loop controls 114 for further manipulating ultra sound image 76. In an embodiment, the user interface provides for random access to any of the active elements through a touch screen. In the one-handed embodiment, the user can use the thumb or any other finger to "touch" and activate any of the screen elements. Since it is through touch panels 102 and 104 that the user accesses and uses the system and process of the present invention, they are further explained in the following FIGUREs.

Monitor 40 displays a graphical user interface, which may have views of fixed formats and/or may give the user the option to retile or rearrange the windows in any fashion desired. The keys and/or buttons of keyboard 106 may be intelligent and interactive and may change their function according to the context, history, and/or state of console 12. Moreoever, in addition to keyboard 106 and touch panels 102 and 104, the present invention may use a microphone for voice activation of all of or any part of the control interface.

In essence, the present invention provides an interface for a three-dimensional volume rendering ultrasound imaging system that presents to the user the necessary hardware and software for generating a three-dimensional volumetrically-rendered ultrasound image of an ultrasound object. The three-dimensional volumetrically-rendered ultrasound image, through the present invention, is manipulable using a number of three-dimensional image compositing functions which are described in greater detail below. The system and method of the present invention present to the user three-dimensional image controls for controlling the three-dimensional volumetrically-rendered ultrasound image that have a visual and operational similarity to two-dimensional image controls for controlling a two-dimensional ultrasound image. A benefit here is that those users who are familiar with the known two-dimensional systems and processes can more readily use the newer three-dimensional ultrasound imaging systems. The present invention further relates the three-dimensional ultrasound image controls to the three-dimensional image compositing functions for manipulating the three-dimensional volumetrically-rendered ultrasound image of the ultrasound object. Moreover, the present invention presents to the user three-dimensional image responses from operation of the three-dimensional ultrasound image controls. The image responses are similar to image responses of a two-dimensional ultrasound imaging system and controlling the three-dimensional volumetrically-rendered ultrasound images using the three-dimensional compositing functions.

In another embodiment of the invention, there is provided an interface for a three-dimensional ultrasound imaging system with a user. The particular embodiment generates a three-dimensional volumetrically-rendered ultrasound image of fluid flow relating to an ultrasound object, said three-dimensional volumetrically-rendered ultrasound image being manipulable using a plurality of three-dimensional image compositing functions. The method and system present to the user a three-dimensional color image control for controllably manipulating said three-dimensional volumetrically-rendered ultrasound image using said plurality of three-dimensional image compositing functions. The three-dimensional image compositing functions are selected from the group of such functions. The group of such functions consists essentially of (1) a color flow mapping function for mapping fluid flow relating to said ultrasound object; (2) a color flow overlay function for mapping fluid flow direction relating to said ultrasound object; (3) a depth-based velocity visualization color mapping function for mapping fluid flow depth relating to said ultrasound object; and (4) an absolute velocity representation function for mapping absolute fluid flow velocity relating to said ultrasound object.

The method and system of the present invention present to the user the color flow overlay function for mapping fluid flow direction relating to said ultrasound object as an overlay function of overlaying forward and reverse flows, thereby generating in real-time color combinations arising from said overlaying. Moreover, the invention may present to the user the depth-based velocity visualization color mapping function for mapping fluid flow depth relating to said ultrasound object. In this function, a light color associates with a physically closer velocity relative to a predetermined observation point and darker color associates with physically farther velocity away from said observation point. Still further, the present invention may present to the user said an absolute velocity representation function for mapping absolute fluid flow velocity relating to said ultrasound object wherein absolute velocity representation function uses absolute velocity to represent the structure, size and position of flow pathologies associated with said ultrasound object, said absolute velocity being independent of flow direction.

FIG. 6 shows in yet further detail primary touch panel 102, secondary touch panel 104, and monitor 40. The display of monitor 40 includes a frequency fusion icon 103, an operational status indicator region 105, and a color bar and baseline indicator portion 107. Operational status indicator region 105, for example, may include indications of operations such as the preprocessing operation, color persist characteristics, and post processing operations. Moreover, operational status indicator region 105 may show the packet size and filter, as well as characteristics relating to the particular color map in use. Color bar and baseline indicator portion 107 shows the mean highest velocity toward and away from the transducer, as well as other information relating to the operation of the transducer 14.

Primary touch panel 102 contains system-specific controls. Secondary touch panel 104 contains mode-specific controls, as well as less frequently used system-specific controls. System controls, such as presets, tools, physio, and probes are located on the touch panel 102. Imaging modalities, such as 2d, mode, color, pulsed wave, continuous wave, and Angio appear on the primary right touch panel 102. Touch panels provide controls that highlight the respective control to indicate the control is active. To turn off an active (highlighted) control, the user touches it. Additional touch and rotary controls pertaining to the selected modality also may appear on the primary right touch panel 104.

FIG. 6 further shows rotary controls 109 that permit adjusting various controls appearing in the touch panels appearing above them. Using rotary controls 109, the present embodiment permits changing the associated values by turning the controls to the right or to the left. These indications and associated controls are explained in greater detail in the on-line and otherwise available manuals for the SONOS 5500 and 7500 by Philips Medical Systems, as well as similar systems by other manufacturers. Since it is through touch panels 102 and 104, and in particular secondary touch panel 104 that the control of the present invention occurs, these are described in further detail below.

FIGS. 7, 8, 9 show in further detail the aspects of the present invention for controlling the compositing of data associated with three-dimensional volumetric rendering of an ultrasound object image. In FIG. 7 there appears secondary touch screen 104, which presents the primary three-dimensional color preview controls. These include 2D control 120 and color control 122. Biplane control icon 132, color suppress control 136, and baseline control 138 have no effect on three-dimensional image control, but are used for two-dimensional image control only. Baseline control unwraps aliased signals to show higher velocities flowing in one direction by lowering color assignments for velocities flowing in the other direction. 3D color control 124 cancels three-dimensional color operation. Acquire control 126, when activated, proceeds with three-dimensional color acquisition using the processes of the present invention.

In the lower portion of the three-dimensional preview controls screen of FIG. 7, gain control 144 affects not only two-dimensional color gain, but also three-dimensional color gain in the 3D mode of operation. Gain control 144 adjusts system sensitivity to received color flow signals. Increasing the color gain percentage increases the amount of color displayed. Gain control 144 is particularly important in three-dimensional image analysis, because it affects both the signal to noise ratio and the data to noise ratio. Fusion control 146 affects the BW fusion, including three-dimensional BW fusion. Fusion optimizes frequencies for penetration, texture or resolution. With Fusion control changes are reflected in the frequency fusion icon. Control of focus control 140 affects the transmit focus in both two-dimensional and three-dimensional operation, both in color, as well as BW operation.

Scale control 142 affects the pulse repetition frequency in both two-dimensional and three-dimensional operation. Control of low velocity sensitivity and frame rate occurs using scale control 142. Also aliasing control is achieved through the use of scale control 142. Scale control 142 changes the range of color flow velocities. The user may lower the scale to see slow flow, and increase it to see higher velocities. Filter control 128 affects the Doppler Wall filter, which is important for three-dimensional operation. Filter control 128 removes low-level signals and reduces noise in the image. Filter modes through Filter control 128 allow the user to apply various filters either during data acquisition and/or while viewing the data. For example, filters that smooth the data, high pass, low pass, and notch filters may be used to filter out noise or data that is not of interest. Focus control 140 repositions the acoustic depth of the color focal zone. When adaptive flow is on, the focus chooses the optimal color frequency.

FIG. 8 presents the secondary three-dimensional color preview controls through which the user operations the system and process of the present invention. As with FIG. 7, the secondary three-dimensional color preview controls include 2D control 120 and color control 122. Secondary controls further include 2nd'ary Controls control 158 and ECG Trigger control 154. Secondary Controls control 158 allows the user to switch between the primary and secondary touch panels. When the control is highlighted, the secondary controls are active. Those controls that affect two-dimensional color only include Map Invert control 160, smoothing control 162, and Map control 165. Full cycle control 156 trades off acquisition time (e.g., the number of beats of a heart) against the number of frames for the ultrasonic image. Packet control affects the ensemble length sensitivity versus the image frame rate. High density control 148 affects the volume size relative to the resolution and sensitivity of the data collection. Agile control 150 permits selection of the RF color frequency between 2.5 and 3.2 MHz. Finally, power control 152 affects sensitivity and should be set to 0.0 dB.

FIG. 9 shows the three-dimensional color controls that a user access for the loop display function. In FIG. 9, 2D control 120 and Map Invert control 160 relate to two-dimensional operation. Smoothing control 162 affects only the smoothing in the three-dimensional color mode of operation. Loop Display control 168 turns off loop display and three-dimensional color operation. Filter control 128 control the Doppler wall filter and permits the user to control the trade of between flash and low velocity operations. Color Controls control 170 allow the user to toggle between primary and secondary in the "Cine Loop Display" mode of operation. Baseline control 138 works best in the first of the C Vision control 174 modes described below.

During three-dimensional color operation, Gain control 144, which affects color opacity, is not as important as in the case of controlling the three-dimensional BW gain. Color Suppress control 136 permits the user to see only non-compromised three-dimensional BW gain. Alternatively, BW Suppress control 172 permits the user to see only three-dimensional color imagery without influence from BW signals. BW suppress control 172 suppresses the black and white image that appears outside of the color image, thus increasing the frame rate. For further C Vision control, FIG. 9 shows C Vision gain control 145 and compress control 147.

Color imaging includes a color mode that uses color to represent the mean velocity and direction of either blood flow as a color flow or tissue as a Doppler signal. Different shades of colors in a defined color spectrum represent different velocities and directions of blood or tissue movement within the selected color area. Color flow is usually used to examine blood flow through valves or pathological orifices in the heart, or through vessels of the body. Accordingly, C Vision control 174 of the present invention provides the valuable option of selecting from four different color visions, each providing very different view of a three-dimensional volumetrically rendered ultrasound image. These include in the present embodiment Color Vision 1, Color Vision 2, Color Vision 3, and Color Vision 4. Color Vision 1 uses traditional color flow mapping to represent blood flow direction and velocity. Color Vision 2 provides enhanced visualization of flow direction by overlaying forward and reverse flows. As such, in Color Vision 2 colors can be produced that are not visible on the color bar. Color Vision 3 shows velocity and uses enhanced color mapping for better visualization of depth cues. In Color Vision 3, for example, enhanced lighter colors represent closer velocities, while darker, more saturated colors represent velocity farther away.

Finally, Color Vision 4 is similar to the two-dimensional Power Angio function of the SONOS 7500 System by Philips Medical Systems. Power Angio is an "amplitude-only" mode that translates the magnitudes of returning ultrasound echoes into shades of a single color. It is used mostly with contrast imaging, because it is more sensitive to reactions of contrast-agent micro bubbles that are struck by ultrasound. Accordingly, Color Vision 4 uses absolute velocity to represent the structure, size and position of flow pathologies. In particular, Color Vision 4 is best used when flow direction is not critical. Thus, through the operation of the single C Vision control 174, the present invention provides a robust set of color controls that facilitate understanding and using the three-dimensional volumetrically rendered ultrasound image data.

In the preferred embodiment, C Vision control 174 affects the color compositing algorithm. For each of the four C Vision settings, the present invention uses four different compositing algorithms. Color Vision 1 uses a classical setting wherein the color compositing process composites only one scalar value per voxel, using, in one embodiment, aliased signal processing techniques, which would be familiar to one skilled in the art of processing Doppler or color flow information. Color Vision 2 uses a process that results in a view that mimics a propane torch flame, where one can see a hotter inner blue flame encompassed within the cooler outer red flame. Color Vision 2 differentiates between positive velocities that are toward transducer 14 and reverse velocities that are away from transducer 14. So, each color voxel is described by two scalar values, a forward value or a reverse value. These are separately composited to form a merged image in an RGB space. Hence, blue reverse flow might overlay red forward flow to achieve an appearance similar to that of a propane flame.

Color Vision 3 provides the ability to change the hue of the velocity depending upon the distance from the viewer to the flow velocity voxel. Like the Color Vision 2, Color Vision 3 uses two separate compositing channels. Velocity signals close to the viewer are composited into the first compositing channel, whereas velocity signals far from the viewer are composited into the second compositing channel. By comparing the ratio of the signals in the 2 composited channels, the display algorithm can infer the average distance of the flow velocity signal from the viewer, and can then change the color hue on the displayed image to indicate that distance. Color Vision 4 creates an Angio-like display by compositing the absolute values of the velocities, and treating them as one would treat an unsigned value such as BW compositing.

An important aspect of C Vision control 174 of the present invention relates to its compositing function. The compositing function relates to the projection or creation of a two-dimensional image based upon the user's three-dimensional perspective in viewing a three-dimensional data matrix. The present invention includes a threshold function that determines what voxels are to be composited. Values below the threshold are made transparent, and will not contribute to the resultant image. In the present invention, the opacity relates to the weighting slope of those values greater than the threshold.

A high opacity (or slope) would result in a bi-stable image, where either voxels were either totally transparent or totally opaque. This would have the effect that a user would not see any voxels "behind" an opaque voxel, as seen along a ray cast line from the viewer's perspective. Alternatively, a low opacity, or slope, would result in a soft, ghosted like image, where all voxels above the threshold would provide equal contribution to the composited ray cast, such as if they were averaged. Such an image might resemble, for example, an x-ray.

FIG. 10 shows graphical user interface panel 176, which an application developer of the live three-dimensional color system of the present invention may access, but which the general user does not access. Notice the complexity and the plurality of controls required to control three-dimensional color flow. For operation of the present invention, the controls indicated with the "+" sign are collapsed into the single C Vision control 174 of FIG. 9.

The present invention makes use of a color map wherein a velocity index, typically from −128 to +127, represents a velocity. With this mapping, an index may be established such that for each of a set of 256 velocity entries a unique RGB values which would result in the color seen on monitor. In one embodiment, the present invention further provides a display brightness control. This provides the user with the ability to override the color mapping function to further enhance the perceived brightness of the RGB value associated with a single velocity index.

Another embodiment of the invention includes a voxel write priority function that serves a key aspect of compositing. With this function, each voxel (whether color or BW) has the ability to block the light reaching the voxels behind it from the viewer's perspective. Note that with volumetric rendering, each spatial voxel has both a BW anatomical value and a color velocity functional value. In one simple scheme, one of the values (either BW or color) would win the voxel. This affects the resulting ultrasound image 76. This decision is based upon each voxel type value, and can be altered by this control. A high weighting toward color flow would imply that more color information would be seen at the expense of black and white. The present invention may provide to vary this weighting as desired.

Still another aspect of the present invention includes a map write priority and additive mapping function. As it turns out, both types of voxel data (color and BW) are composited to separate two-dimensional planes. These two planes are merged to form a single RGB image for the display. One method is to simply add the RGB values. This is sometimes referred to as additive mapping. Another approach uses selective mapping, where only one type (BW or color) wins the pixel. The present invention, therefore, provides a map write priority that, in addition to the individual pixel values (BW and Color), enables determining which plane an individual voxel will use.

The present invention also modulates other available user controls. For example, depending upon the particular color compositing algorithm in use, it may be desirable to influence other available user controls, such as wall filter and smoothing controls, in such a way so as to not have to adjust these other controls when switching from to the different C Vision controls 172. To accomplish this, the present invention provides "offsets" so that these user controls could be modulated without the user knowing. These offsets, for example, may include (1) a wall filter control 128 offset, (2) a smoothing control 162 offset; and (3) a color compositing gain control 145 offset.

A further aspect of the present invention includes the use of two-dimensional color Doppler controls for three-dimensional ultrasound imaging. Color Doppler gain control in two-dimensional ultrasound imaging affects the front-end gain of the Doppler echoes received from red blood cells (or other moving structures in the body). This control allows the user to trade off noise, which may be seen as random color pixels against low amplitude Doppler echoes. In three-dimensional imaging, the present invention maps color Doppler gain control to both three-dimensional voxel opacity and to three-dimensional display brightness. By modifying the control, the user may affect three-dimensional opacity, but without having to make direct adjustment Low voxel weightings, as controlled by opacity, result in a dimmer, less bright image. Higher gain helps to emphasize the flow, and increased weight was given to penetrating through black and white. The present invention, therefore, modulates four different internal parameters (opacity, brightness, color compositing gain, and write-priority) through three-dimensional color gain control to give the illusion that the control acts as it would in two-dimensional color ultrasound imaging.

Another aspect of the present invention includes the use of the Wall Filter, which is a commonly used control for two-dimensional ultrasound imaging. In two-dimensional ultrasound imaging, the filter control 128 effects a high pass filter. According to the Doppler equation, low velocities correspond to low Doppler shifted frequencies, and high velocities correspond to high frequencies. Therefore, a high pass filter is required for color flow imaging to eliminate the large slow moving echoes coming from the moving blood echoes. By making such a filter variable, the user may optimally select between flash suppression (echoes from slow moving tissue) and the ability to detect motion from the slower velocity red blood cells. The present invention achieves the appearance and effect of the wall filter control in three-dimensional imaging by modifying the compositing threshold. As such, with the present invention, lower velocity signals can be rejected (or accepted) in the volume composited image by the user who varies the three-dimensional Filter control 128. Although this requires different programming and software module interfaces, the present invention achieves a result similar to the results perceived in two-dimensional ultrasound imaging.

Therefore, the present invention provides a number of ways to present to the user a graphical interface providing power processes for displaying and controlling three-dimensional volumetrically rendered ultrasound images. The processes, however, are based, if only in perception, on processes with which the user may be familiar. This is due to the fact that the presentation of the display intentionally relates to presentations with which a person skilled in two-dimensional sonography may be familiar. Accordingly, the present invention makes three-dimensional sonography, real-time and pre-recorded, much more practical than has previously been the case.

Figure 11:
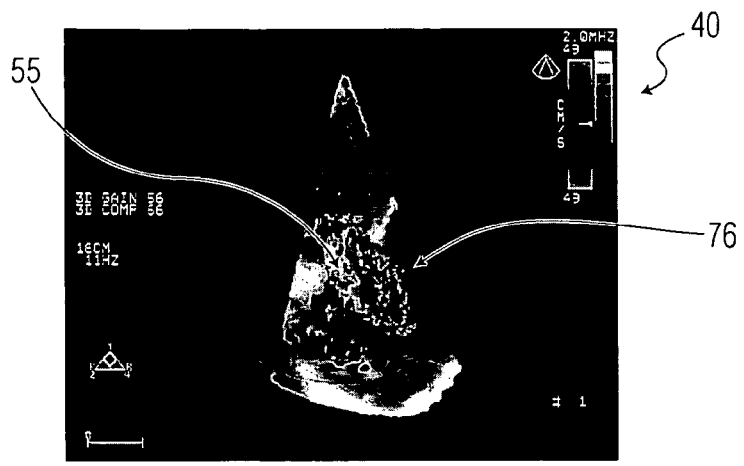
Figure 12:
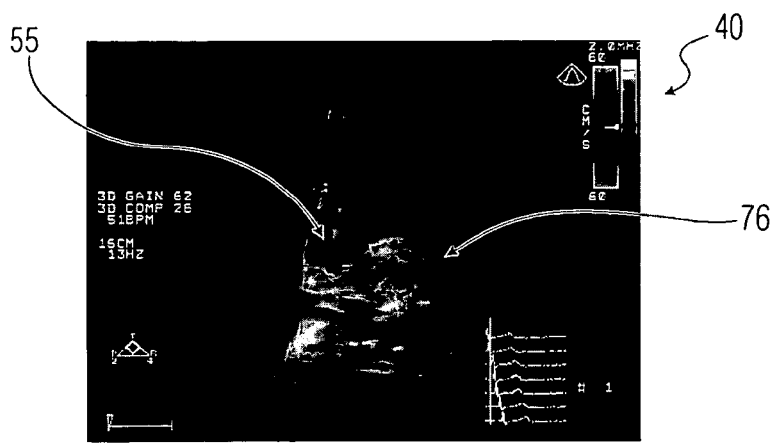
Figure 13:
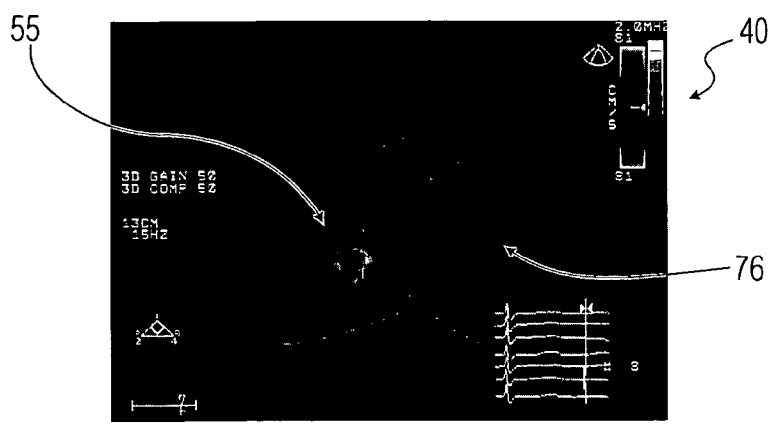
Figure 14A:
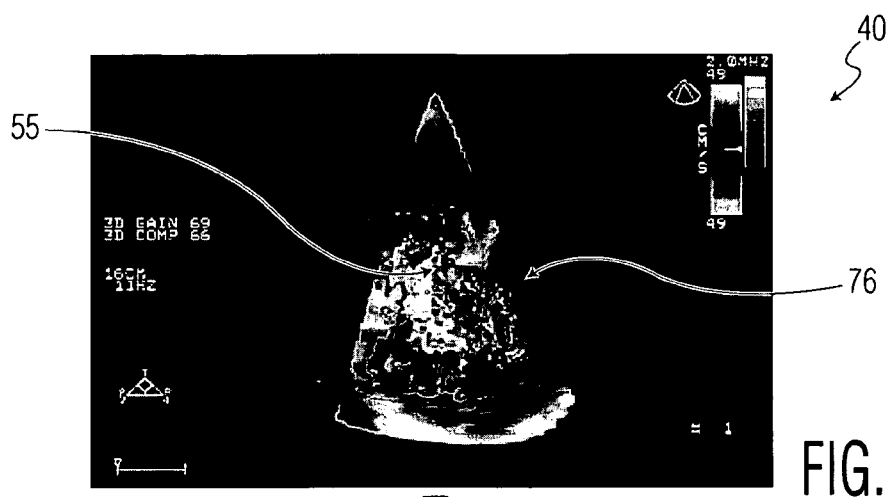
Figure 14C:
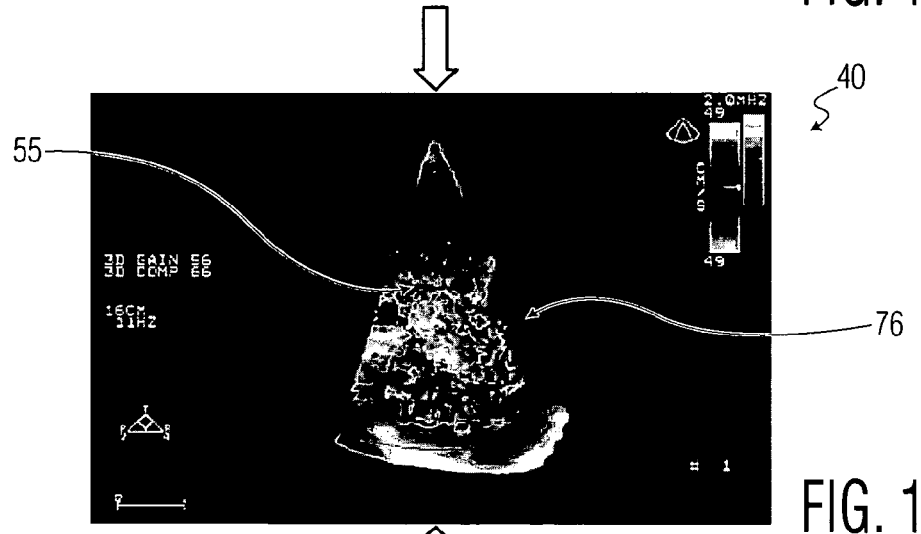
Figure 14B:
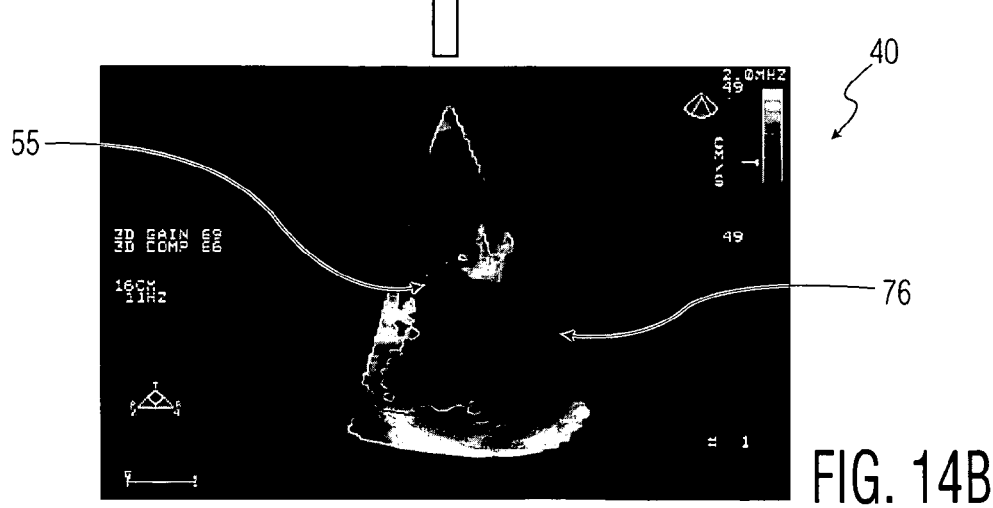
Figure 15:
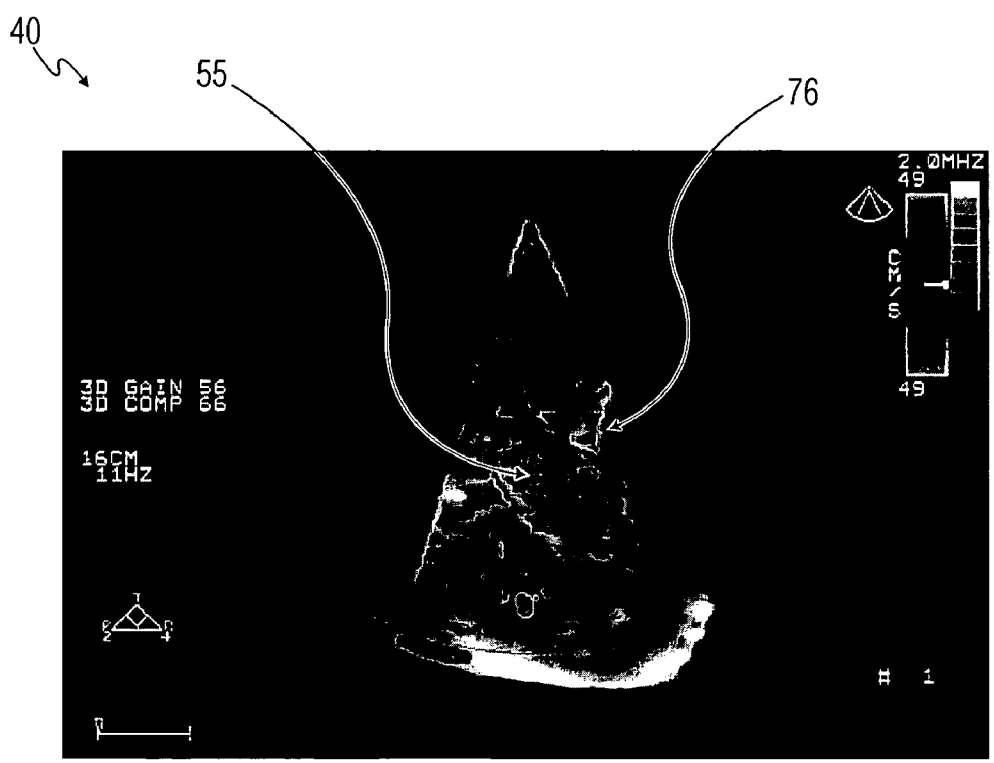

To illustrate these achievements, FIGS. 11 through 15 are monitor displays 40 for the various functions and capabilities of the present invention. Thus, FIG. 11 shows a monitor 40 display for the output of Color Vision 1, as described above, which shows ultrasound image 76 including color area 55 as a more classical view where traditional color flow mapping represents blood flow direction and velocity. FIGS. 12 and 13 exhibit ultrasound image 76 including color area 55 the enhanced visualization of flow direction of Color Vision 2, showing forward color flow in FIG. 12 and reverse flow in FIG. 13. FIGS. 14A through 14C illustrate in ultrasound image 76 including color area 55 the effect of Color Vision 3, as herein described, wherein there appear in FIG. 14A a near velocity measurement, FIG. 14B a far velocity measurement, and FIG. 14C the composite of the images from FIGS. 14A and 14B. FIG. 15 presents ultrasound image 76 including color area 55 from the here described Color Vision 4 function, wherein absolute velocity portrays the structure, size and position of blood flow pathologies. As is apparent from the fact that all of the displays in FIGS. 11 through 15 are of the same ultrasound object, the present invention provides a wide variety of possible ultrasound image display potentials.

Although the invention has been described with reference to specific embodiments, it will be understood by those skilled in the art that various changes may be made and equivalents may be substituted for elements thereof without departing from the true spirit and scope of the invention. Accordingly, it is to be understood that the embodiments of the invention herein described are merely illustrative of the application of the principles of the invention. Reference herein to details of the illustrated embodiments, therefore, is not intended to limit the scope of the claims, which themselves recite those features regarded as essential to the invention.

The invention claimed is:

1. A method for interfacing a three-dimensional ultrasound imaging system with a user, comprising the steps of:
   generating a multi-color three-dimensional volumetrically-rendered ultrasound image of an ultrasound object, said multi-color three-dimensional volumetrically-rendered ultrasound image manipulable using a plurality of multi-color three-dimensional image compositing functions;
   presenting to the user a plurality of multi-color three-dimensional image controls for controlling said multi-color three-dimensional volumetrically-rendered ultrasound image;
   presenting the user with a plurality of three-dimensional image responses from operation of said three-dimensional ultrasound image controls;
   automatically offsetting selected three-dimensional ultrasound image controls so as to cause said three-dimensional image responses to simulate responses for two-dimensional ultrasound image controls; and
   relating said plurality of multi-color three-dimensional ultrasound image controls to control said plurality of multi-color three-dimensional image compositing functions for manipulating said multi-color three-dimensional volumetrically-rendered ultrasound image of said ultrasound object.

2. The method of claim 1, further comprising the step of automatically offsetting a wall filter control associated as one of said automatically offset three-dimensional image controls.

3. The method of claim 1, further comprising the step of automatically offsetting a smoothing control associated as one of said automatically offset three-dimensional image controls.

4. The method of claim 1, further comprising the step of automatically offsetting a color compositing gain control associated as one of said automatically offset three-dimensional image controls.

5. A system for interfacing a three-dimensional ultrasound imaging system with a user, the system comprising:
   means for generating a multi-color three-dimensional volumetrically-rendered ultrasound image of an ultrasound object, said multi-color three-dimensional volumetrically-rendered ultrasound image manipulable using a plurality of multi-color three-dimensional image compositing functions;
   means for presenting a plurality of three-dimensional image controls for controlling said multi-color three-dimensional volumetrically-rendered ultrasound image;
   means for presenting the user with a plurality of three-dimensional image responses from operation of said three-dimensional ultrasound image controls;
   means for automatically offsetting selected three-dimensional ultrasound image controls so as to cause said three-dimensional image responses to simulate responses for two-dimensional ultrasound image controls; and
   means for relating said plurality of multi-color three-dimensional ultrasound image controls to said plurality of multi-color three-dimensional image compositing functions for manipulating said multi-color three-dimensional volumetrically-rendered ultrasound image of said ultrasound object.

6. The system of claim 5, further comprising instructions for automatically offsetting a wall filter control associated as one of said automatically offset three-dimensional image controls.

7. The system of claim 5, further comprising instructions for automatically offsetting a smoothing control associated as one of said automatically offset three-dimensional image controls.

8. The system of claim 5, further comprising instructions for automatically offsetting a color compositing gain control associated as one of said automatically offset three-dimensional image controls.

9. A storage medium storing thereon processor-readable instructions for interfacing a three-dimensional ultrasound imaging system with a user, the instructions causing the processor to execute a method comprising:
   generating a multi-color three-dimensional volumetrically-rendered ultrasound image of an ultrasound object, said multi-color three-dimensional volumetrically-rendered ultrasound image being manipulable using a plurality of multi-color three-dimensional image compositing functions;
   presenting to the user a plurality of multi-color three-dimensional image controls for controlling said a three-dimensional volumetrically-rendered ultrasound image;
   presenting the user with a plurality of three-dimensional image responses from operation of said three-dimensional ultrasound image controls;
   automatically offsetting selected three-dimensional ultrasound image controls so as to cause said three-dimensional image responses to simulate responses for two-dimensional ultrasound image controls; and relating said plurality of three-dimensional ultrasound image controls to said plurality of three-dimensional image compositing functions for manipulating said three-dimensional volumetrically-rendered ultrasound image of said ultrasound object.

10. The storage medium of claim 9, wherein the method further comprises storing the state of at least one of said three-dimensional ultrasound imaging system controls at a predetermined time and in a format for subsequent recall of both the state of the three-dimensional volumetrically-rendered ultrasound image and the associated state of three-dimensional ultrasound imaging system controls.

* * * * *